United States Patent [19]

Pettit

[11] Patent Number: 5,883,120

[45] Date of Patent: Mar. 16, 1999

[54] ANTIFUNGAL ACTIVITY OF THE SPONGISTATINS

[75] Inventor: George R. Pettit, Paradise Valley, Ariz.

[73] Assignee: Arizona Board of Regents, a body corporate, acting on behalf of Arizona State University, Tempe, Ariz.

[21] Appl. No.: 876,407

[22] Filed: Jun. 16, 1997

[51] Int. Cl.$^6$ .......................... A61K 31/335; A61K 31/34
[52] U.S. Cl. ............................................ 514/450; 514/462
[58] Field of Search ...................................... 514/450, 462

[56] References Cited

U.S. PATENT DOCUMENTS

| | | | |
|---|---|---|---|
| 5,328,929 | 7/1994 | Pettit et al. | 514/482 |
| 5,393,897 | 2/1995 | Pettit et al. | 549/267 |
| 5,436,400 | 7/1995 | Pettit et al. | 549/267 |

*Primary Examiner*—Raymond Henley, III
*Attorney, Agent, or Firm*—Richard R. Mybeck; Peter B. Scull

[57] ABSTRACT

This invention relates generally to the field of antifungal agents and a pharmaceutical preparation containing those agents which appear to be potentially useful in the field of antifungal therapy. More particularly, this invention relates to the discovery of remarkably unexpected properties for a series of macrocyclic lactone polyethers (spongistatins) which are derived from the marine sponges Spongia sp. and *Spirastrella spinispirulifera* and which inhibited growth of yeasts and filamentous fungi in disk diffusion and broth macrodilution (for spongistatin 1) assays. Spongistatins 2–7 likewise demonstrated antifungal activity in disk diffusion methods. Therapeutic dosage forms are also described for the treatment of infections caused by *Candida Albicans, Cryptococcus neoformans, Candida lusitaniae, Candida parapsilosis, Candida tropicalis, Candida glabrata, Issatchenkia orientalis, Rhodotorula mucilaginosa, Aspergillus fumigatus, Rhizopus ologosporus*, and other yeast and filamentous fungi including strains resistant to amphotericin B, ketoconazole and flucytosine.

10 Claims, 2 Drawing Sheets

ANTIFUNGAL ACTIVITY OF THE SPONGISTATINS

This research was funded in part by Outstanding Investigator Grant CA 44344-01-09 awarded by the National Cancer Institute, DHHS. The United States government may have certain rights to this invention.

This application discloses and claims only subject matter disclosed in prior provisional pending U.S. patent application, Ser. No. 60/020,008 filed Jun. 18, 1996 for ANTIFUNGAL ACTIVITY OF THE SPONGISTATINS.

This invention relates generally to the discovery of very potent antifungal activity for spongistatin 1 and the related spongistatins (2 through 7, inclusive) which are hereinafter described in detail. More particularly, this invention relates to the discovery of new and unexpected antifungal properties for a series of macrocyclic lactone polyethers (spongistatins) which have heretofore been isolated from the marine sponges Spongia sp. and *Spirastrella spinispirulifera*. These unexpected properties include inhibition of the growth of the opportunistic fungi *Candida albicans* and *Cryptococcus neoformans* in disk diffusion and broth macrodilution assays. In broth macrodilution assays, spongistatin 1 was fungicidal for *C. albicans, C. neoformans, C. lusitaniae, C. parapsilosis, C. tropicalis, C. glabrata, Issatchenkia orientalis, Rhodotorula mucilaginosa, Aspergillus fumigatus, Rhizopus ologosporus*, and other yeast and filamentous fungi including strains resistant to amphotericin B, ketoconazole and flucytosine. At 35° C., spongistatin 1 appeared to induce an altered germ tube morphology in *C. albicans*.

BACKGROUND OF THE INVENTION

Marine organisms are proving to be very productive sources of new therapeutic agents. Indeed, some of today's most promising anticancer drugs in clinical or preclinical trials have been isolated from marine invertebrates or their associated microbes. (Flam, F. 1994. Chemical prospectors scour seas for promising drugs. Science 266:1324–1325; Pettit, G. R. 1994. Marine animal and terrestrial plant anticancer constituents. Pure & Appl. Chem. 66:2271–2281). The spongistatins are a family of macrocyclic lactone polyethers recently isolated from marine Porifera. Spongistatins 1–3 were discovered in Eastern Indian Ocean Spongia sp. (Pettit, G. R., Z. A. Cichacz, F. Gao, C. L. Herald, and M. R. Boyd. 1993). Isolation and structure of the remarkable human cancer cell growth inhibitors spongistatins 2 and 3 from an Eastern Indian Ocean Spongia sp. J. Chem. Soc. Chem. Commun. 14:1166–1168; Pettit, G. R., Z. A. Cichacz, C. L. Herald, M. R. Boyd, J. M. Schmidt, and J. N. A. Hooper. 1993. Isolation and structure of spongistatin 1. J. Org. Chem. 58:1302–1304), and spongistatins 4–7 in the Southeast African marine sponge, *Spirastrella spinispirulifera*. (Pettit, G. R., C. L. Herald, Z. A. Cichacz, F. Gao, M. R. Boyd, N. D. Christie, and J. M. Schmidt. 1993. Antineoplastic agents 293. The exceptional human cancer cell growth inhibitors spongistatins 6 and 7. Nat. Prod. Lett. 3:239–244; Pettit, G. R., Z. A. Cichacz, F. Gao, J. M. Schmidt, M. R. Boyd, N. D. Christie, and F. E. Boettner. 1993. Isolation and structure of the powerful human cancer cell growth inhibitors spongistatins 4 and 5 from an African *Spirastrella spinispirulifera* (Porifera). J. Chem. Soc. Chem. Commun. 24:1805–1807). All of the spongistatins have exceptionally potent and selective inhibitory activity against a subset of the U.S. National Cancer Institute's human cancer cell lines. (Pettit, G. R., Z. A. Cichacz, F. Gao, C. L. Herald, and M. R. Boyd. 1993. Isolation and structure of the remarkable human cancer cell growth inhibitors spongistatins 2 and 3 from an Eastern Indian Ocean Spongia sp. J. Chem. Soc. Chem. Commun. 14:1166–1168; Pettit, G. R., Z. A. Cichacz, C. L. Herald, M. R. Boyd, J. M. Schmidt, and J. N. A. Hooper. 1993. Isolation and structure of spongistatin 1. J. Org. Chem. 58:1302–1304; Pettit, G. R., C. L. Herald, Z. A. Cichacz, F. Gao, M. R. Boyd, N. D. Christie, and J. M. Schmidt. 1993. Antineoplastic agents 293. The exceptional human cancer cell growth inhibitors spongistatins 6 and 7. Nat. Prod. Lett. 3:239–244; and Pettit, G. R., Z. A. Cichacz, F. Gao, J. M. Schmidt, M. R. Boyd, N. D. Christie, and F. E. Boettner. 1993. Isolation and structure of the powerful human cancer cell growth inhibitors spongistatins 4 and 5 from an African *Spirastrella spinispirulifera* (Porifera). J. Chem. Soc. Chem. Commun. 24:1805–1807).

The isolation and elucidation of spongistatins 1–7 are described in U.S. Pat. Nos. 5,328,929 (2, 3, 4 & 6), 5,393,897 (5 and 7 inter alia), and 5,436,400 (1).

Because of their availability, it was of interest to determine whether these macrocyclic lactones might also have other interesting therapeutic activity. The increase in antibiotic resistant microbes and our paucity of effective antifungals, in addition to a growing population of immunocompromised patients, indicated a critical need for novel antimicrobial agents and it was with this goal in mind that we discovered the antifungal activity of the spongistatins.

DESCRIPTION OF THE PREFERRED EMBODIMENT

Figure 1:
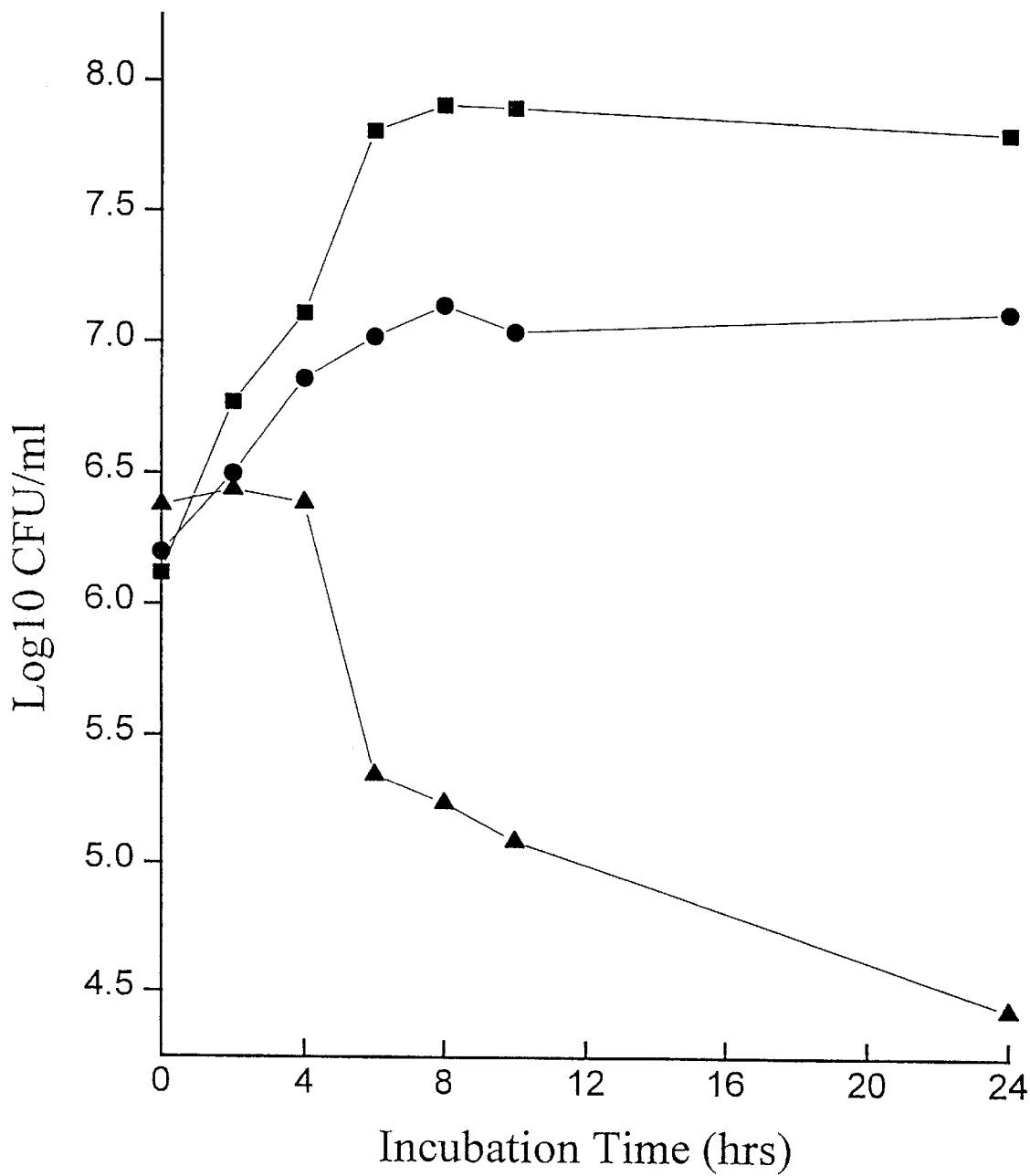
FIG. 1 is the killing kinetics of spongistatin 1 with no drug (squares) and at 1X (circles) and 2X (triangles) the MIC for *C. albicans*.

A source of spongistatins 1–7 was located at the Arizona State University Cancer Research Institute, Tempe, Ariz.

Antimicrobial activity was assayed by both broth macrodilution and disk susceptibility tests according to methods established by the National Committee for Clinical Laboratory Standards. (National Committee for Clinical Laboratory Standards. 1990. Approved standard M2-A4. Performance standards for antimicrobic disk susceptibility tests. National Committee for Clinical Laboratory Standards, Villanova, Pa.; National Committee for Clinical Laboratory Standards. 1994. Reference method for broth dilution antifungal susceptibility testing of yeasts; Tentative standard. NCCLS document M27-T. National Committee for Clinical Laboratory Standards, Villanova, Pa.). In the disk diffusion assay, Mueller-Hinton agar was used for susceptibility testing of *Staphylococcus aureus* (ATCC #29213), *Enterococcus faecalis* (ATCC #29212) and *Escherichia coli* (ATCC #25922), Gonococcal Typing agar for *Neisseria gonorrhoeae* (ATCC #49226) and YM agar for *Candida albicans* (ATCC #90028) and *Cryptococcus neoformans* (ATCC #90112). Inocula were adjusted to a density of 0.10 at 625 nm, and 100 µl (*S. aureus, E. faecalis, N. gonorrhoeae*) or 50 µl (*E. coli, C. albicans, C. neoformans*) spread on the appropriate plates. Excess moisture was allowed to absorb for 10 minutes before applying disks. Immediately prior to the assay, spongistatins 1–7 were reconstituted in sterile dimethylsulfoxide, and two-fold dilutions applied to sterile 6 mm disks. Disks were dried at 37° C., and applied to inoculated plates. Test plates of E. coli, S. aureus and E. faecalis were incubated at 37° C., N. gonorrhoeae at 37° C. with 5% $CO_2$, and C. albicans and C. neoformans at 25° C. Zones of inhibition were recorded after 16 hours for bacterial cultures, and 42 hours for fungal cultures. The MIC was defined as the lowest concentration of drug resulting in a clear zone of growth inhibition.

At concentrations up to 100 µg/disk, the spongistatins did not inhibit growth of the two Gram-negative and two Gram-positive bacteria tested. However, all of the spongistatins inhibited growth of the opportunistic fungi C. albicans and C. neoformans (Table 1). Overall, spongistatin 1 was the most potent compound, and this is consistent with the relative cytotoxicities of the spongistatins against human cancer cell lines, (Pettit, G. R., Z. A. Cichacz, F. Gao, C. L. Herald, and M. R. Boyd. 1993. Isolation and structure of the remarkable human cancer cell growth inhibitors spongistatins 2 and 3 from an Eastern Indian Ocean Spongia sp. J. Chem. Soc. Chem. Commun. 14:1166–1168; Pettit, G. R., Z. A. Cichacz, C. L. Herald, M. R. Boyd, J. M. Schmidt, and J. N. A. Hooper. 1993. Isolation and structure of spongistatin 1. J. Org. Chem. 58:1302–1304; Pettit, G. R., C. L. Herald, Z. A. Cichacz, F. Gao, M. R. Boyd, N. D. Christie, and J. M. Schmidt. 1993. Antineoplastic agents 293. The exceptional human cancer cell growth inhibitors spongistatins 6 and 7. Nat. Prod. Lett. 3:239–244; and Pettit, G. R., Z. A. Cichacz, F. Gao, J. M. Schmidt, M. R. Boyd, N. D. Christie, and F. E. Boettner. 1993. Isolation and structure of the powerful human cancer cell growth inhibitors spongistatins 4 and 5 from an African Spirastrella spinispirulifera (Porifera). J. Chem. Soc. Chem. Commun. 24:1805–1807), and their antimitotic activities. (Bai, R., Z. A. Cichacz, C. L. Herald, G. R. Pettit, and E. Hamel. 1993. Spongistatin 1, a highly cytotoxic, sponge-derived, marine natural product that inhibits mitosis, microtubule assembly, and the binding of vinblastine to tubulin. Molec. Pharmacol. 44:757–766; Bai, R., G. F. Taylor, Z. A. Cichacz, C. L. Herald, J. A. Kepler, G. R. Pettit, and E. Hamel. 1995. The spongistatins, potently cytotoxic inhibitors of tubulin polymerization, bind in a distinct region of the Vinca domain. Biochem. 34:9714–9721). Spongistatin 1 is the most abundant [3.4× $10^{-7}$% yields (Pettit, G. R., Z. A. Cichacz, C. L. Herald, M. R. Boyd, J. M. Schmidt, and J. N. A. Hooper. 1993. Isolation and structure of spongistatin 1. J. Org. Chem. 58:1302–1304)] of the lactone polyethers isolated from Spongia sp. and Spirastrella spinispirulifera.

The antifungal activity of spongistatin 1 was also tested by the broth macrodilution assay (National Committee for Clinical Laboratory Standards. 1994. Reference method for broth dilution antifungal susceptibility testing of yeasts; Tentative standard. NCCLS document M27-T. National Committee for Clinical Laboratory Standards, Villanova, Pa.). C. albicans and C. neoformans were maintained at 35° C. on YM agar, and inocula prepared as recommended in document M27-T. Tests were performed in sterile 12×75 mm plastic tubes containing two-fold dilutions of spongistatin 1 (reconstituted in DMSO) in 0.165M morpholinepropanesulfonic acid buffered RPMI 1640 medium (pH 7.0). Tubes were incubated without agitation at 35° C. Minimum inhibitory concentrations (MICs) were determined after 48 hours for C. albicans and 72 hours for C. neoformans. The MIC was defined as the lowest concentration of spongistatin 1 that inhibited all visible growth of the test organism. Minimum fungicidal concentrations (MFCs) were determined by subculturing 0.1 ml from each tube with no visible growth in the MIC broth macrodilution series onto a drug-free YM plate. The plates were incubated at 35° C. for 24 hours for C. albicans, and 48 hours for C. neoformans. The MFC was defined as the lowest concentration of antifungal that completely prevented growth on YM plates. The MICs and MFCs of spongistatin 1 were 6.25 µg/ml for C. albicans, and 3.12 µg/ml for C. neoformans. That spongistatin 1 inhibited fungi in two radically different susceptibility assays, disk diffusion and broth macrodilution, may be predictive of in vivo effectiveness.

Figure 2:
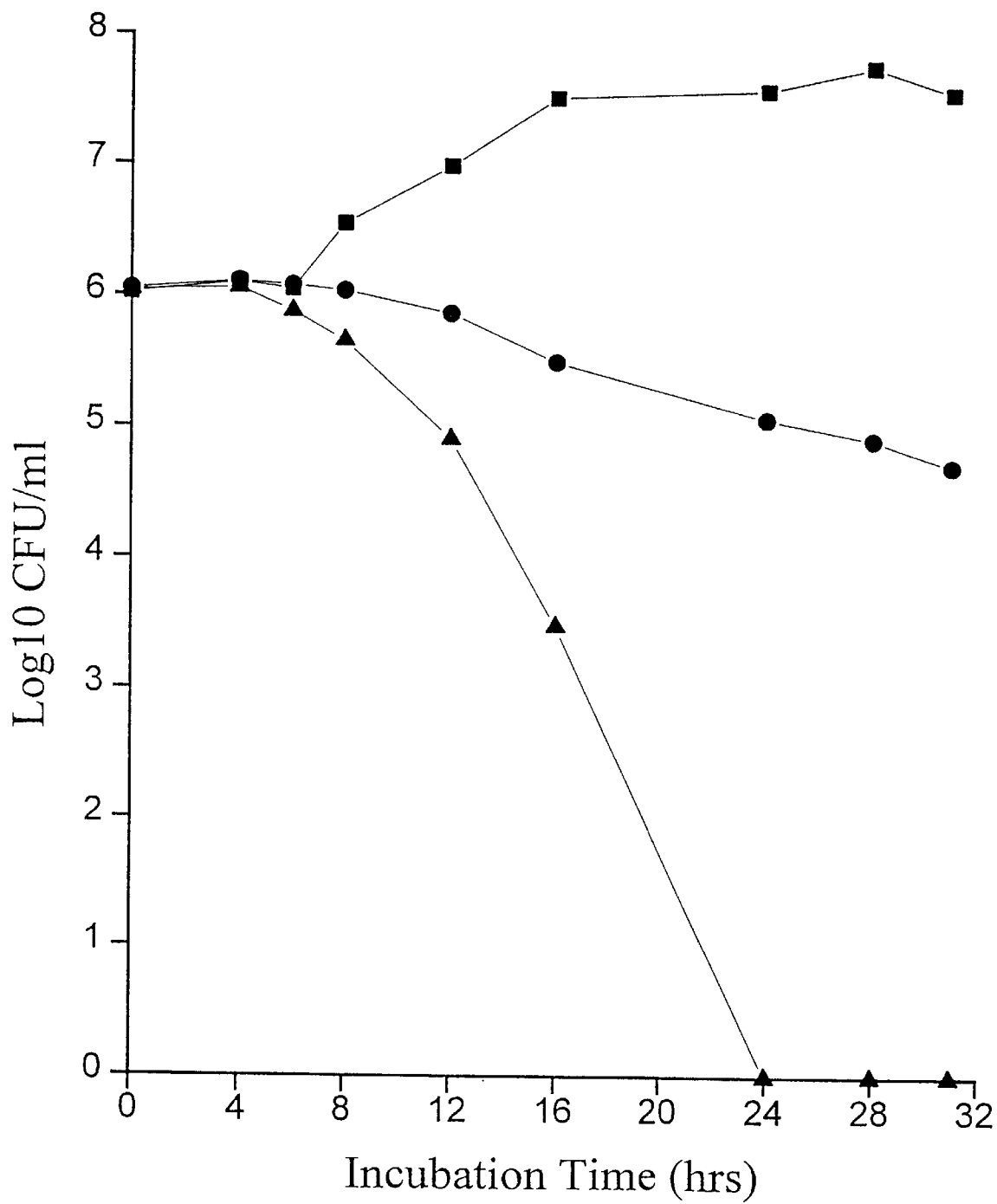
FIG. 2 is the killing kinetics of spongistatin 1 with no drug (squares) and at 1X (circles) and 2X (triangles) the broth macrodilution MIC for *C. neoformans*.

The fungicidal activity of spongistatin 1 for two of the opportunistic yeasts was confirmed in killing kinetics studies. These experiments demonstrated that spongistatin 1 was fungicidal for C. albicans and C. neoformans at 2X MIC (FIGS. 1 and 2). Spongistatin 1 at 2X MIC caused a 1 $\log_{10}$ reduction in the cfu/ml of C. albicans after 6 hours of incubation, and after 12 hours of incubation for C. neoformans. After 24 hours at 2X MIC, there was a 2 $\log_{10}$ reduction in C. albicans cfu/ml, and no viable C. neoformans.

Throughout the killing kinetics experiments, yeast cells were the predominant morphologic form in untreated C. albicans cultures. However, from 6 hours on elongated structures predominated in 2X MIC treated cultures. The most abundant elongated forms more closely resembled germ tubes than hyphae. No obvious morphological alterations in spongistatin 1 treated C. neoformans were observed.

Tubulin, the major component of microtubules, is the target of many naturally occurring compounds that cause cells to arrest in mitosis. (Hamel, E. 1990. Interactions of tubulin with small ligands, p. 89–191. In J. Avila (ed.), Microtubule Proteins. CRC Press, Boca Raton, Fla.). Recently, marine mollusks and sponges containing novel antimitotic agents have been described. (Bai, R., S. J. Friedman, G. R. Pettit, and E. Hamel. 1992. Dolastatin 15, a potent antimitotic depsipeptide derived from Dolabella auricularia: interaction with tubulin and effects on cellular microtubules. Biochem. Pharmacol. 43:2637–2645; Bai, R., K. D. Paull, C. L. Herald, L. Malspeis, G. R. Pettit, and E. Hamel. 1991. Halichondrin B and homohalichondrin B, marine natural products binding in the Vinca domain of tubulin: discovery of tubulin-based mechanism of action by analysis of differential cytotoxicity data. J. Biol. Chem. 266:15882–15889). In mammalian cells, spongistatin 1 has also been shown to be antimitotic. In kangaroo rat kidney PtK1 cells, spongistatin 1 caused the accumulation of cells arrested in mitosis, and the disappearance of intracellular microtubules. (Bai, R., Z. A. Cichacz, C. L. Herald, G. R. Pettit, and E. Hamel. 1993. Spongistatin 1, a highly cytotoxic, sponge-derived, marine natural product that inhibits mitosis, microtubule assembly, and the binding of vinblastine to tubulin. Molec. Pharmacol. 44:757–766). Spongistatin 1 also inhibited the glutamate-induced polymerization of purified bovine brain tubulin. (Bai, R., Z. A. Cichacz, C. L. Herald, G. R. Pettit, and E. Hamel. 1993. Spongistatin 1, a highly cytotoxic, sponge-derived, marine natural product that inhibits mitosis, microtubule assembly, and the binding of vinblastine to tubulin. Molec. Pharmacol. 44:757–766). Our observations of abnormal cell division in spongistatin 1 treated C. albicans led us to determine that this compound may also affect fungal tubulin.

The structures of spongistatins 1–7, the macrocyclic lactone polyethers isolated from Spongia sp. (spongistatins 1–3) and Spirastrella spinispirulifera (spongistatins 4–7) are shown below:

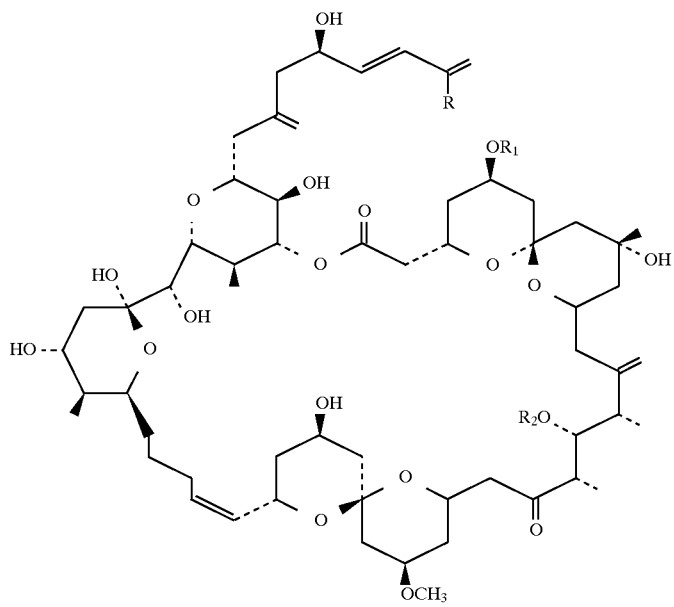

Spongistatin 1, R = Cl, R₁ = R₂ = COCH₃
Spongistatin 2, R = H, R₁ = R₂ = COCH₃
Spongistatin 3, R = Cl, R₁ = H, R₂ = COCH₃
Spongistatin 4, R = Cl, R₁ = COCH₃, R₂ = H
Spongistatin 6, R = H, R₁ = COCH₃, R₂ = H

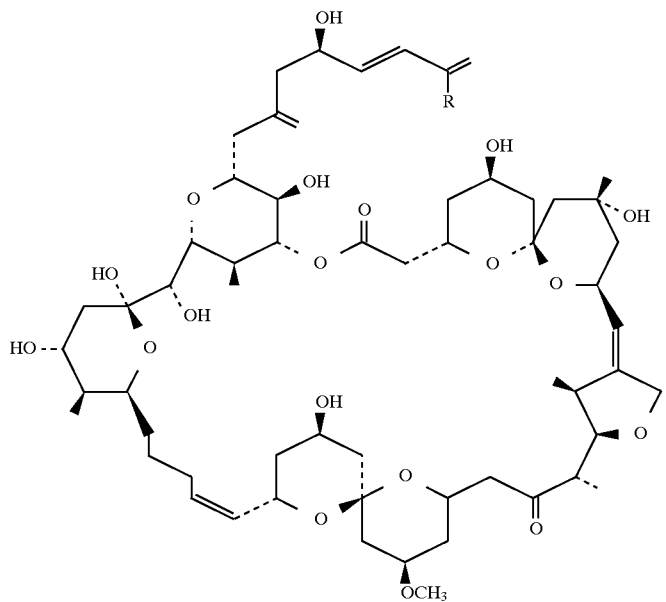

Spongistatin 5, R = Cl
Spongistatin 7, R = H

Spongistatin 1, R=Cl, $R_1$=$R_2$=COCH$_3$
Spongistatin 2, R=H, $R_1$=$R_2$=COCH$_3$
Spongistatin 3, R=Cl, $R_1$=H, $R_2$=COCH$_3$
Spongistatin 4, R=Cl, $R_1$=COCH$_3$, $R_2$=H
Spongistatin 6, R=H, $R_1$=COCH$_3$, $R_2$=H
Spongistatin 5, R=Cl
Spongistatin 7, R=H The antifungal activity of spongistatin 1 in broth macrodilution and disk diffusion methods are reported in Table I, below.

TABLE I

| Organism | Broth Macrodilution method | | Disk Diffusion method |
|---|---|---|---|
| | MIC (μg/ml) | MFC (μg/ml) | MIC (μg/disk) |
| Candida albicans | 6.25 | 6.25 | 6.25–12.5 |
| Cryptococcus neoformans | 3.12 | 3.12 | 6.25–12.5 |

The antifungal activity of spongistatins 2–7 using the disk diffusion assay are reported in Table II, below:

TABLE II

| Compound | Candida albicans | MIC (μg/disk) Cryptococcus neoformans |
|---|---|---|
| Spongistatin 2 | 25–50 | 50–100 |
| Spongistatin 3 | 25–50 | 50–100 |
| Spongistatin 4 | 12.5–25 | 6.25–12.5 |
| Spongistatin 5 | 25–50 | 6.25–12.5 |
| Spongistatin 6 | 25–50 | 12.5-25 |
| Spongistatin 7 | 6.25–12.5 | 12.5-25 |

In testing, Spongistatins 1–7 were reconstituted in sterile dimethylsulfoxide (DMSO) immediately prior to all assays. DMSO alone had no detectable inhibitory effect on any of the tested microbes.

Spongistatin 1 was then tested against a diverse collection of yeast and filamentous fungi, several of which are antibiotic resistant. Yeast strains (listed in Table IV) were maintained by single colony transfer on Yeast Morphology (YM) agar (Difco) at 35° C. ATCC#32354 is flucytosine resistant, ATCC#64124 is ketoconazole resistant and ATCC#42720 is amphotericin B resistant. *Issatchenkia orientalis* was formerly classified as *Candida krusei*, and *Rhodotorula mucilaginosa* as *Rhodotorula rubra* (ATCC product literature). Filamentous fungi (Table IV) were maintained on Potato Dextrose Agar (PDA) slants at 35° C.

Spongistatin 1 was screened against yeasts by the broth macrodilution assay according to the NCCLS (1994). Antibiotic resistant strains were subcultured only once after acquisition to ensure no loss of antibiotic resistance. Yeasts were suspended and diluted as recommended to yield final inocula ranging from $0.5–2.5 \times 10^3$ cfu/ml. Tests were performed in sterile 12×75 mm plastic tubes containing two-fold dilutions of spongistatin 1 in 0.165M morpholinepropanesulfonic acid (MOPS)-buffered RPMI 1640 medium (pH 7.0). One tube was left drug-free for a turbidity control. Tubes were incubated without agitation at 35° C. MICs were determined after 48 hours for all yeast strains except Cryptococcus, which was read after 72 hours. The MIC was defined as the lowest concentration of spongistatin 1 that inhibited all visible growth of the test organism.

Minimum fungicidal concentration (MFCs) were determined by subculturing 0.1 ml from each tube with no visible growth in the MIC broth macrodilution series onto drug-free YM plates. The plates were incubated at 35° C. for 24 hours for all yeast strains except Cryptococcus, which was incubated 48 hours. The MFC was defined as the lowest concentration of spongistatin 1 that completely inhibited growth on YM plates.

Broth macrodilution susceptibility testing of *Aspergillus fumigatus* and *Rhizopus oligosporus* was performed according to a proposed standardized procedure (Espinel-Ingroff et al. 1997) with slight modification. To induce conidium and sporangiospore formation, *A. fumigatus* R. and oligosporus were grown on PDA slants at 35° C. for 6 days. Fungal slants were covered with 1 ml sterile 0.85% NaCl, and suspensions made by gently probing the colonies with the tip of a sterile pipette. The resulting mixture of hyphal fragments and conidia or sporangiospores was withdrawn, transferred to a sterile clear microfuge tube, and heavy particles allowed to settle for 10 minutes. The upper homogeneous suspension was transferred to a sterile microfuge tube, vortexed 15 s, adjusted spectrophotometrically, and diluted in sterile 0.165M MOPS buffered RPMI 1640 medium, pH 7.0, to yield final inocula ranging from $0.5–2.5 \times 10^3$ cfu/ml. Susceptibility to spongistatin 1 was then determined by broth macrodilution assays as described above for the yeast cultures. MICs for the filamentous fungi were read after 24 hours, aliquots were aseptically removed for dilution plating and microscopy and MFCs read 24 hours later. In broth macrodilution tests, spongistatin 1 was fungicidal for all yeast and filamentous fungi examined, including flucytosine-resistant *C. albicans*, ketoconazole-resistant *C. albicans* and amphotericin B-resistant *C. lusitaniae* (Table III).

TABLE III

Antifungal activity of spongistatin 1 in the broth macrodilution assay.

| Organism | ATCC # | MIC (μg/ml) | MFC (μg/ml) |
|---|---|---|---|
| Candida albicans | 90028 | 6.25 | 6.25 |
| Candida albicans | 14053 | 3.12 | 25 |
| Candida albicans | 32354 | 3.12 | 3.12 |
| Candida albicans | 64124 | 6.25 | 6.25 |
| Candida albicans | 60193 | 3.12 | 3.12 |
| Candida lusitaniae | 42720 | 1.56 | 12.5 |
| Candida parapsilosis | 22019 | 6.25 | 25 |
| Candida tropicalis | 750 | 1.56 | 12.5 |
| Candida glabrata | 90030 | 1.56 | 12.5 |
| Issatchenkia orientalis | 6258 | 6.25 | 25 |
| Cryptococcus neoformans | 90112 | 3.12 | 3.12 |
| Cryptococcus neoformans | 66031 | 0.195 | 1.56 |
| Rhodotorula mucilaginosa | 90030 | 1.56 | 12.5 |
| Aspergillus fumigatus | 96918 | 12.5 | 12.5 |
| Rhizopus ologosporus | 22959 | 6.25 | 6.25 |

Based upon the foregoing observations, these compositions are believed useful in the treatment of one or more fungal infections, such as Aspergillosis, Candidiasis or thrush, internal infections such as cryptococcosis, epidermal infections, infections caused by antibiotic resistant fungi and the like. Similar fungal infections are enumerated in the *AMA Home Medical Encyclopedia* published by Random House, Inc. 1989.

The dosage administered will be dependent upon the identity of the fungus; the location of the fungal infection; the type of host involved; the nature of concurrent treatment, if any; and the frequency of treatment specified.

Illustratively, dosage levels of the administered active ingredients are: intravenous, 0.1 to about 200 μg/kg; orally, 5 to about 1000 μg/kg of host body weight.

Expressed in terms of concentration, an active ingredient can be present in the compositions of the present invention for localized use about the cutis, intranasally, pharyngolaryngeally, bronchially, intravaginally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in salves and ointments for topical application although unit dosage forms, such as tablets, capsules, pills, powders, suppositories, sterile parenteral solutions or suspensions, sterile non-parenteral solutions or suspensions, lozenges and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the active ingredient can be dissolved in a suitable vehicle for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the vaginal routes can be utilized particularly in the treatment of by means of a suppository. A vehicle which has a melting point at about body temperature or one that is readily soluble can be utilized. For example, cocoa butter and various polyethylene glycols (Carbowaxes) can serve as the vehicle.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

In a preferred practice for the treatment of dermatological fungi, the active ingredient will be delivered to the site as an ointment or salve which will comprise water and oil emulsion as the principal carrier. Other conventional ingredients, when conditions and aesthetics dictate, include petrolatum and mineral oil, lipophilic solubilizers such as polyethylene glycol, carbowax, moisturizers such as lanolin and fragrance.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antifungal agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies one of the compound designated as "spongistatin"; specifically, spongistatin 1 through spongistatin 7, inclusive.

COMPOSITION "A"

Hard-Gelatin Capsules

One thousand two-piece hard gelatin capsules for oral use, each capsule containing 200 μg of an active ingredient are prepared from the following types and amounts of ingredients:

| | |
|---|---|
| Active ingredient, micronized | 200 g |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a fungal disease by the oral administration of one or two capsules one to four times a day.

Using the procedure above, capsules are similarly prepared containing an active ingredient in 50, 250 and 500 μg amounts by substituting 50 μg, 250 μg and 500 μg of an active ingredient for the 200 μg used above.

COMPOSITION "B"

Soft Gelatin Capsules

One-piece soft gelatin capsules for oral use, each containing 200 μg of an active ingredient, finely divided by means of an air micronizer, are prepared by first suspending the compound in 0.5 ml of corn oil to render the material capsulatable and then encapsulating in the above manner.

The foregoing capsules are useful for treating a fungal disease by the oral administration of one or two capsules one to four times a day.

COMPOSITION "C"

Tablets

One thousand tablets, each containing 200 μg of an active ingredient, are prepared from the following types and amounts of ingredients:

| Active ingredient, micronized | 200 g |
|---|---|
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 μg of the active ingredient.

The foregoing tablets are useful for treating a fungal disease by the oral administration of one or two tablets one to four times a day.

Using the procedure above, tablets are similarly prepared containing an active ingredient in 250 μg and 100 μg amounts by substituting 250 μg and 100 μg of an active ingredient for the 200 μg used above.

COMPOSITION "D"

Oral Suspension

One liter of an aqueous suspension for oral use, containing in each teaspoonful (5 ml) dose, 50 μg of an active ingredient, is prepared from the following types and amounts of ingredients:

| Active ingredient, micronized | 10 g |
|---|---|
| Citric acid | 2 g |
| Benzoic acid | 1 g |
| Sucrose | 790 g |
| Tragacanth | 5 g |
| Lemon Oil | 2 g |
| Deionized water, q.s. 1000 ml | |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a fungal disease at a dose of 1 teaspoonful (15 ml) three times a day.

COMPOSITION "E"

Parenteral Product

One liter of a sterile aqueous suspension for parenteral injection, containing 30 μg of an active ingredient in each milliliter for treating a fungal disease, is prepared from the following types and amounts of ingredients:

| Active ingredient, micronized | 30 g |
|---|---|
| POLYSORBATE 80 | 5 g |
| Methylparaben | 2.5 g |
| Propylparaben | 0.17 g |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a fungal disease at a dose of 1 milliliter (1 ml) three times a day.

COMPOSITION "F"

Vaginal Suppository

One thousand suppositories, each weighing 2.5 g and containing 200 μg of an active ingredient are prepared from the following types and amounts of ingredients:

| Active ingredient, micronized | 15 g |
|---|---|
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted vaginally for treating candidiasis (thrush).

COMPOSITION "G"

Intranasal Suspension

One liter of a sterile aqueous suspension for intranasal instillation, containing 20 μg of an active ingredient in each milliliter, is prepared from the following types and amounts of ingredients:

| Active ingredient, micronized | 15 g |
|---|---|
| POLYSORBATE 80 | 5 g |
| Methylparaben | 2.5 g |
| Propylparaben | 0.17 g |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a fungal disease, by intranasal instillation of 0.2 to 0.5 ml given one to four times per day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a fungal disease, at localized sites by applying a powder one to four times per day.

COMPOSITION "I"

Oral Powder

One hundred grams of an active ingredient in bulk form is finely divided by means of an air micronizer. The micronized powder is divided into individual doses of 200 µg and packaged.

The foregoing powders are useful for treating a fungal disease, by the oral administration of one or two powders suspended in a glass of water, one to four times per day.

COMPOSITION "J"

Insufflation

One hundred grams of an active ingredient in bulk form is finely divided by means of an air micronizer.

The foregoing composition is useful for treating a fungal disease, by the inhalation of 300 µg one to four times a day.

COMPOSITION "K"

Ointment

One hundred grams of an active ingredient in bulk form is finely divided by means of an air micronizer. The micronized powder is them admixed into a water and oil emulsion with the addition of suitable moisturizers and fragrances as desired.

The foregoing ointment is useful for treating a fungal disease by one topical application of the ointment on the affected area as needed, preferably at least twice a day.

From the foregoing, it becomes readily apparent that a new and useful antifungal agent and new and useful antifungal preparations have been herein described and illustrated which fulfill the aforestated object in a remarkably unexpected fashion. It is further believed that the spongistatin can be utilized as probes to examine fungal cell biochemistry including morphogenesis and cell division. It is, of course, understood that such modifications, alterations and adaptions as will readily occur to the artisan confronted with this disclosure are intended within the spirit of the present invention which is limited only by the scope of the claims appended hereto.

Accordingly, what is claimed is:

1. A method of treating a yeast or filamentous fungi-induced infection in a host afflicted with yeast or filamentous fungi-induced infections comprising administering to said host an effective amount of an active ingredient selected from the group consisting of Spongistatin 1, Spongistatin 2, Spongistatin 3, Spongistatin 4, Spongistatin 5, Spongistatin 6, and Spongistatin 7 in a pharmaceutically acceptable carrier.

2. The method according to claim 1 in which said fungi is Candida Albicans, *Cryptococcus neoformans, Candida lusitaniae, Candida parapsilosis, Candida tropicalis, Candida glabrata, Issatchenkia orientalis, Rhodotorula mucilaginosa, Aspergillus fumigatus, Rhizopus ologosporus,* and *fungi resistant to flucytosine, ketoconazole and amphotericin B.*

3. The method according to claim 1 in which said fungi induced infections are Candidiasis, Aspergillosis, Cryptococcosus, epidermal infections, systemic infections and the like.

4. The method according to claim 3 in which said active ingredient is administered parenterally.

5. The method according to claim 3 in which said active ingredient is administered topically.

6. The method according to claim 3 in which said active ingredient is administered intravenously.

7. The method according to claim 3 in which said active ingredient is administered in a suppository.

8. The method according to claim 5 in which said active ingredient is delivered in a carrier comprising a water and oil emulsion, petrolatum, mineral oil, a moisturizer, a solubilizer and fragrance.

9. The method according to claim 1 in which said fungi is yeast.

10. The method according to claim 1 in which said fungi is filamentous.

* * * * *